United States Patent
Mitsui et al.

Patent Number: 6,118,026
Date of Patent: *Sep. 12, 2000

[54] STABILIZER FOR (FLUOROARYL)BORANE COMPOUND AND METHODS OF STABILIZING AND CRYSTALLIZING (FLUOROARYL)BORANE COMPOUND

[75] Inventors: Hitoshi Mitsui, Kitakatsuragi-gun; Tsunemasa Ueno, Ikeda; Ikuyo Ikeno, Osaka; Naoko Yamamoto, Nishinomiya, all of Japan

[73] Assignee: Nippon Shokubai Co., Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/104,042

[22] Filed: Jun. 25, 1998

[30] Foreign Application Priority Data

Jul. 4, 1997 [JP] Japan .................... 9-180118

[51] Int. Cl.⁷ .................................. C07C 5/02

[52] U.S. Cl. .................................. 568/6; 568/1

[58] Field of Search .................................. 568/1, 6

[56] References Cited

U.S. PATENT DOCUMENTS

| | | | |
|---|---|---|---|
| 5,510,536 | 4/1996 | Ikeda | 568/6 |
| 5,545,759 | 8/1996 | Ikeda | 568/6 |

FOREIGN PATENT DOCUMENTS

| | | |
|---|---|---|
| 0 604 963 A1 | 7/1994 | European Pat. Off. . |
| 0 728 761 A2 | 8/1996 | European Pat. Off. . |
| WO 98/22475 | 5/1998 | WIPO . |

OTHER PUBLICATIONS

"Perfluorophenyl Derivatives of the Elements I. Tris(pentafluorophenyl)boron", A.G. Massey et al., Journal of Organometallic Chemistry, J. Organometal Chem., 2(1964), pp. 245–250.

Aldrich chemical catalogue p. 903, 1996.

Susan Budavari et al., The Merck Index 11 Ed, Merck & Co., Inc. Dec. 29, 1989 p 871, col. 1 ¶ 5409; XP–002100310.

*Primary Examiner*—Jean F Vollano
*Attorney, Agent, or Firm*—Nixon & Vanderhye PC

[57] ABSTRACT

A (fluoroaryl)borane compound expressed by General Formula (1):

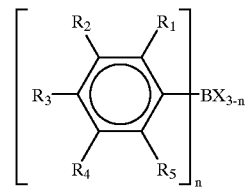

where each of $R_1$–$R_5$ represents a hydrogen atom, a fluorine atom, a hydrocarbon group, or an alkoxy group, provided that at least one of $R_1$–$R_5$ represents a fluorine atom, X represents a fluorine atom, a chlorine atom, a bromine atom, or an iodine atom, and n represents 2 or 3, is stabilized by letting inorganic metal salts having a fluorine atom coexist with the (fluoroaryl)borane compound in a hydrocarbon solution. After the hydrocarbon solution is concentrated in the presence of the inorganic metal salts, the inorganic metal salts are removed and the fluoroaryl)borane compound is crystallized. Consequently, it has become possible to provide a method of stabilizing a (fluoroaryl)borane compound by suppressing the decomposition reaction while the solution is heated and concentrated, stored (preserved), or transported/transferred, and a crystallizing method of isolating highly-pure crystals (powders) of the (fluoroaryl)borane compound efficiently.

11 Claims, No Drawings

STABILIZER FOR (FLUOROARYL)BORANE COMPOUND AND METHODS OF STABILIZING AND CRYSTALLIZING (FLUOROARYL)BORANE COMPOUND

FIELD OF THE INVENTION

The present invention relates to a stabilizer and a stabilizing method which can stabilize a (fluoroaryl)borane compound, such as tris(fluoroaryl)borane and bis (fluoroaryl)boryl halide, serving as, for example, an excellent co-catalyst for a metallocene catalyst (polymeric catalyst) used in a cation complex polymerization reaction, and to a crystallizing method of the (fluoroaryl)borane compound.

BACKGROUND OF THE INVENTION

A (fluoroaryl)borane compound, amongst of all, tris(pentafluorophenyl)borane, is an useful compound as a co-catalyst for promoting the activity of a metallocene catalyst (polymeric catalyst) used in a cation complex polymerization reaction. The metallocene catalyst has been receiving considerable attentions as a polyolefin polymeric catalyst.

J. Organomet. Chem., 2, 245 (1964) discloses an example method of taking out crystals (powders) of tris(pentafluorophenyl)borane, wherein a pentane solution of tris(pentafluorophenyl)borane is evaporated to dryness in vacuo at 20° C. However, the yield of tris(pentafluorophenyl)borane produced by the above method out of bromopentafluorobenzene used as a raw material is as low as 30%–50%. In addition, this publication fails to disclose a purity of tris(pentafluorophenyl)borane thus taken out.

Japanese Laid-open Patent Application No. 247978/1994 (Tokukaihei No. 6-247978) discloses a method of crystallizing tris(pentafluorophenyl)borane out of an octane solution of tris(pentafluorophenyl)borane and a method of sublimating a toluene solution of tris(pentafluorophenyl)borane after evaporating the toluene solution to dryness as other example methods of taking out crystals (powders) of tris(pentafluorophenyl)borane. However, the yield of tris(pentafluorophenyl)borane produced by these methods is also as low as 53%–71%.

To take out the crystals (powders) of tris(pentafluorophenyl)borane out of the solution thereof, the solution is usually subjected to the evaporation to dryness or a heating and concentrating manipulation over a long period in the form of a solution. Also, tris(pentafluorophenyl) borane is generally stored (preserved) or transported/transferred in the form of a solution.

However, when tris(pentafluorophenyl)borane is subjected to the evaporation to dryness or the heating and concentrating manipulation over a long period in the form of a solution, it partially decomposes to, for example, pentafluorobenzene. To be more specific, if a solution of tris(pentafluorophenyl)borane is merely heated and concentrated, the above decomposition reaction is triggered and a large amount of pentafluorobenzene resides with tris(pentafluorophenyl)borane as a decomposition product.

In other words, to obtain the crystals of tris(pentafluorophenyl)borane by the conventional methods, the solution must be subjected to the heating and concentrating manipulation over a long period, during which tris(pentafluorophenyl)borane eventually starts to decompose, thereby lowering the purity thereof. Thus, the conventional methods have a problem that highly-pure crystals (powders) of tris(pentafluorophenyl)borane can not be isolated at high yield.

Also, while a solution of tris(pentafluorophenyl)borane is stored (preserved) over a long period, tris(pentafluorophenyl)borane eventually starts to decompose through the above decomposition reaction. Thus, there has been a demand for a method which can store (preserve) tris(pentafluorophenyl)borane over a long period.

SUMMARY OF THE INVENTION

It is therefore a first object of the present invention to provide a stabilizer and a stabilizing method which can stabilize a (fluoroaryl)borane compound by suppressing the decomposition reaction while it is heated and concentrated, stored (preserved), or transported/transferred. Also, it is a second object of the present invention to provide a crystallizing method which can isolate highly-pure crystals (powders) of the (fluoroaryl)borane compound at high yield.

The inventors of the present invention conducted an assiduous study on the stabilizer for and the stabilizing method of the (fluoroaryl)borane compound, as well as the crystallizing method of the (fluoroaryl)borane compound. In due course, they discovered that, although the reason why the function and effect can be achieved is not specifically clear, if inorganic metal salts having a fluorine atom are let coexist with the (fluoroaryl)borane compound in a hydrocarbon solution, the decomposition reaction can be suppressed while a solution of the (fluoroaryl)borane compound is heated and concentrated or stored (preserved) over a long period, thereby making it possible to stabilize the (fluoroaryl)borane compound. Also, the inventors achieved the present invention when they discovered that highly-pure crystals (powders) of the (fluoroaryl)borane compound can be isolated at high yield by crystallizing the (fluoroaryl) borane compound out of a hydrocarbon solution containing the (fluoroaryl)borane compound by concentrating the solution in the presence of inorganic metal salts having a fluorine atom first and thence removing the inorganic metal salts, or by crystallizing the (fluoroaryl)borane compound by cooling a hydrocarbon solution containing the (fluoroaryl)borane compound after the solution has been preserved in the presence of the inorganic metal salts having a fluorine atom and the inorganic metal salts are subsequently removed.

More specifically, to fulfill the first object, a stabilizer of the present invention for a (fluoroaryl)borane compound expressed by General Formula (1):

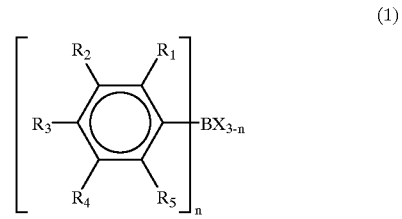

(1)

where each of $R_1$, $R_2$, $R_3$, $R_4$, and $R_5$ represents a hydrogen atom, a fluorine atom, a hydrocarbon group, or an alkoxy group, provided that at least one of $R_1$–$R_5$ represents a fluorine atom, X represents a fluorine atom, a chlorine atom, a bromine atom, or an iodine atom, and n represents 2 or 3, is characterized by containing inorganic metal salts having a fluorine atom.

According to the above arrangement, the stabilizer contains the inorganic metal salts having a fluorine atom. Thus, although the reason why the function and effect can be achieved is not specifically clear, a highly-pure (fluoroaryl)borane compound can be stored (preserved) in a stable manner by adding the stabilizer to the (fluoroaryl)borane compound. More specifically, for example, the decomposition reaction can be suppressed while a solution of the (fluoroaryl)borane compound is heated and concentrated, stored (preserved) over a long period, or transported/transferred, thereby making it possible to stabilize the (fluoroaryl)borane compound readily at low costs.

Also, to fulfill the first object, a method of stabilizing a (fluoroaryl)borane compound expressed by General Formula (1) above of the present invention is characterized in that inorganic metal salts having a fluorine atom are let coexist with the (fluoroaryl)borane compound in a hydrocarbon solution.

According to the above method, a highly-pure (fluoroaryl)borane compound can be stabilized. In other words, the decomposition reaction can be suppressed while a solution of the (fluoroaryl)borane compound is heated and concentrated, stored (preserved) over a long period, or transported/transferred. Consequently, the (fluoroaryl)borane compound can be stabilized readily at low costs.

Further, to fulfill the first object, a method of preserving and transporting a (fluoroaryl)borane compound expressed by General Formula (1) above of the present invention is characterized in that a hydrocarbon solution containing the (fluoroaryl)borane compound is preserved or transported in the presence of inorganic metal salts having a fluorine atom.

According to the above method, a highly-pure (fluoroaryl)borane compound can be preserved or transported. In other words, the decomposition reaction can be suppressed, and therefore, the (fluoroaryl)borane compound can be preserved or transported readily at low costs.

To fulfill the second object, a method of crystallizing a (fluoroaryl)borane compound out of a hydrocarbon solution, which contains the (fluoroaryl)borane compound and inorganic metal salts having a fluorine atom and has been preserved and transported by the above method, is characterized in that the (fluoroaryl)borane compound is crystallized by cooling the solution after having removed the inorganic metal salts.

Also, to fulfill the second object, a method of crystallizing the (fluoroaryl)borane compound expressed by General Formula (1) above out of a hydrocarbon solution containing the (fluoroaryl)borane compound of the present invention is characterized in that the (fluoroaryl)borane compound is crystallized by concentrating the hydrocarbon solution in the presence of inorganic metal salts having a fluorine atom first and thence removing the inorganic metal salts.

According to the above method, the decomposition reaction of the (fluoroaryl)borane compound can be suppressed, and therefore, highly-pure crystals (powders) of the (fluoroaryl)borane compound can be readily isolated at high yield and low costs. In addition, since the crystallized (fluoroaryl)borane compound can be handled in the form of solid, not only the handling property during the storage (preservation) or transportation/transfer can be improved, but also the costs of storage (preservation) or transportation/transfer can be saved compared with the conventional case where the (fluoroaryl)borane compound is handled in the form of a solution.

Further objects, features, advantages of the present invention will be fully understood by the following description. Also, the benefits of the present invention will be apparent from the following explanation.

DESCRIPTION OF THE EMBODIMENTS

In the present invention, "the hydrocarbon solution containing the (fluoroaryl)borane compound" includes a hydrocarbon solution containing the (fluoroaryl)borane compound in a suspended state, that is, a hydrocarbon solution containing slurry of the (fluoroaryl)borane compound.

The stabilizer of the present invention for the (fluoroaryl)borane compound expressed by General Formula (1) above contains inorganic metal salts having a fluorine atom. Also, the stabilizing method of the present invention is a method, wherein the inorganic metal salts having a fluorine atom are let coexist with the (fluoroaryl)borane compound expressed by General Formula (1) above in a hydrocarbon solution. Further, the crystallizing method of the present invention is a method of crystallizing the (fluoroaryl)borane compound expressed by General Formula (1) above out of the hydrocarbon solution containing the (fluoroaryl)borane compound by concentrating the solution in the presence of the inorganic metal salts having a fluorine atom first and thence removing the inorganic metal salts; and a method of crystallizing the (fluoroaryl)borane compound expressed by General Formula (1) above out of the hydrocarbon solution containing the (fluoroaryl)borane compound by cooling the solution after the solution has been preserved in the presence of the inorganic metal salts having a fluorine atom and the inorganic metal salts are removed subsequently therefrom.

The (fluoroaryl)borane compound to be stabilized or crystallized in the present invention expressed by the above formula is a compound, in which each of the substituents denoted as $R_1$, $R_2$, $R_3$, $R_4$, and $R_5$ is a hydrogen atom, a fluorine atom, a hydrocarbon group, or an alkoxy group, provided that at least one of $R_1$–$R_5$ is a fluorine atom, the substituent denoted as X is a fluorine atom, a chlorine atom, a bromine atom, or an iodine atom, and n is 2 or 3. Thus, when n=2, the (fluoroaryl)borane compound is bis(fluoroaryl)boryl halide, and when n=3, the (fluoroaryl)borane compound is tris(fluoroaryl)borane.

Examples of the hydrocarbon group include: an aryl group, a straight-chain, branched-chain, or cyclic alkyl group having up to 12 carbon atoms, a straight-chain, branched-chain, or cyclic alkenyl group having 2–12 carbon atoms, etc. The hydrocarbon group may further include a functional group that remains inactive to the stabilizer and the stabilizing and crystallizing methods of the present invention. Examples of such a functional group include: a methoxy group, a methylthio group, an N,N-dimethylamino group, an o-anise group, a p-anise group, a trimethylsilyl group, a t-butyldimethylsilyloxy group, a trifluoromethyl group, etc.

The alkoxy group is expressed by General Formula (A):

$$—OR_a \qquad (A)$$

where $R_a$ represents a hydrocarbon group. Examples of the hydrocarbon group denoted as $R_a$ in the formula include: an aryl group, a straight-chain, branched-chain, or cyclic alkyl group having up to 12 carbon atoms, a straight-chain, branched-chain, or cyclic alkenyl group having 2–12 carbon atoms. The hydrocarbon group may further include a functional group that remains inactive to the stabilizer and the stabilizing and crystallizing methods of the present invention.

Examples of the alkoxy group expressed by General Formula (A) above include: a methoxy group, an ethoxy group, an n-propoxy group, an isopropoxy group, an n-butoxy group, an isobutoxy group, a sec-butoxy group, a t-butoxy group, a cyclohexyloxy group, an allyloxy group, a phenoxy group, etc.

The (fluoroaryl)borane compound can be obtained by, for example, reacting an adequate kind of a (fluoroaryl)

magnesium derivative with boron halide in an ether solvent or the like. If a mole ratio of the (fluoroaryl)magnesium derivative and boron halide is set adequately, either of bis(fluoroaryl)boryl halide or tris(fluoroaryl)borane can be obtained selectively. Also, the hydrocarbon solution containing the (fluoroaryl)borane compound can be readily obtained from an ether solution containing the (fluoroaryl) borane compound by a so-called solvent exchange technique for exchanging an ether solvent with a hydrocarbon solvent. A producing method of the (fluoroaryl)borane compound is not especially limited.

Examples of bis(fluoroaryl)boryl halide include: bis (pentafluorophenyl)boryl halide, bis(2,3,4,6-tetrafluorophenyl)boryl halide, bis(2,3,5,6-tetrafluorophenyl)boryl halide, bis(2,3,5-trifluorophenyl) boryl halide, bis(2,4,6-trifluorophenyl)boryl halide, bis(1,3-difluorophenyl)boryl halide, bis(2,3,5,6-tetrafluoro-4-methylphenyl)boryl halide, bis(2,3,4,6-tetrafluoro-5-methylphenyl)boryl halide, bis(2,4,5-trifluoro-6-methylphenyl)boryl halide, bis(2,3,6-trifluoro-4-methylphenyl)boryl halide, bis(2,4,6-trifluoro-3-methylphenyl)boryl halide, bis(2,6-difluoro-3-methylphenyl)boryl halide, bis(2,4-difluoro-5-methylphenyl)boryl halide, bis(3,5-difluoro-2-methylphenyl)boryl halide, bis(4-methoxy-2,3,5,6-tetrafluorophenyl)boryl halide, bis(3-methoxy-2,4,5,6-tetrafluorophenyl)boryl halide, bis(2-methoxy-3,5,6-trifluorophenyl)boryl halide, bis(3-methoxy-2,5,6-trifluorophenyl)boryl halide, bis(3-methoxy-2,4,6-trifluorophenyl)boryl halide, bis(2-methoxy-3,5-difluorophenyl)boryl halide, bis(3-methoxy-2,6-difluorophenyl)boryl halide, bis(3-methoxy-4,6-difluorophenyl)boryl halide, bis(2-methoxy- 4,6-difluorophenyl)boryl halide, bis(4-methoxy-2,6-difluorophenyl)boryl halide, etc.

Examples of tris(fluoroaryl)borane include: tris (pentafluorophenyl)borane, tris(2,3,4,6-tetrafluorophenyl) borane, tris(2,3,5,6-tetrafluorophenyl)borane, tris(2,3,5-trifluorophenyl)borane, tris(2,4,6-trifluorophenyl) borane, tris(1,3-difluorophenyl) borane, tris(2,3,5,6-tetrafluoro-4-methylphenyl)borane, tris(2,3,4,6-tetrafluoro-5-methylphenyl)borane, tris(2,4,5-trifluoro-6-methylphenyl) borane, tris(2,3,6-trifluoro-4-methylphenyl)borane, tris(2,4, 6-trifluoro-3-methylphenyl) borane, tris(2, 6-difluoro-3-methylphenyl)borane, tris(2,4-difluoro-5-methylphenyl) borane, tris(3, 5-difluoro-2-methylphenyl)borane, tris(4-methoxy-2,3,5,6-tetrafluorophenyl)borane, tris(3-methoxy-2,4,5,6-tetrafluorophenyl)borane, tris(2-methoxy-3,5,6-trifluorophenyl)borane, tris(3-methoxy-2,5,6-trifluorophenyl)borane, tris(3-methoxy-2,4,6-trifluorophenyl)borane, tris(2-methoxy-3,5-difluorophenyl) borane, tris(3-methoxy-2,6-difluorophenyl)borane, tris(3-methoxy-4,6-difluorophenyl)borane, tris(2-methoxy-4,6-difluorophenyl)borane, tris(4-methoxy-2,6-difluorophenyl) borane, etc. Of all these example compounds, tris (pentafluorophenyl) borane is particularly suitable.

The inorganic metal salts having a fluorine atom used for the stabilizer and the stabilizing and crystallizing methods of the present invention are not especially limited as long as being insoluble into the hydrocarbon solvent. However, it is preferable that the above inorganic metal salts have at least one kind of metal selected from the group consisting of transition elements, typical metal elements, and metalloid elements. It is further preferable that the above inorganic metal salts have at least one kind of metal selected from the group consisting of alkali metal and alkali earth metal. The stabilizer of the present invention contains the above inorganic metal salts.

Examples of the inorganic metal salts having a fluorine atom (hereinafter, referred to simply as the inorganic metal salts) include, but not limited to: lithium fluoride, beryllium fluoride, sodium fluoride, magnesium fluoride, aluminium fluoride, potassium fluoride, calcium fluoride, titanium fluoride, vanadium fluoride, chromium fluoride, manganese fluoride, iron fluoride, cobalt fluoride, nickel fluoride, copper fluoride, zinc fluoride, gallium fluoride, germanium fluoride, strontium fluoride, yttrium fluoride, zirconium fluoride, niobium fluoride, molybdenum fluoride, silver fluoride, cadmium fluoride, indium fluoride, tin fluoride, antimony fluoride, tellurium fluoride, cesium fluoride, barium fluoride, cerium fluoride, osmium fluoride, iridium fluoride, mercuric fluoride, lead fluoride, magnesium chloride fluoride, magnesium bromide fluoride, magnesium iodide fluoride, calcium chloride fluoride, calcium bromide fluoride, calcium iodide fluoride, barium chloride fluoride, barium bromide fluoride, barium iodide fluoride, etc. One member or a mixture of two or more members selected from these example inorganic metal salts can be used effectively. Of all these examples, lithium fluoride and magnesium bromide fluoride are particularly suitable.

An amount of added inorganic metal salts can be set adequately depending on a combination of the (fluoroaryl) borane compound and inorganic metal salts, etc, and is not especially limited. However, to stabilize the (fluoroaryl) borane compound effectively, it is preferable to set a mole ratio of the inorganic metal salts to the (fluoroaryl)borane compound to 0.1 or greater, more preferably, to a range between 0.5 and 10.0 inclusive, and most preferably, to a range between 0.7 and 5.0 inclusive.

As has been explained, since the stabilizer of the present invention includes the inorganic metal salts, although the reason why the function and effect can be achieved is not specifically clear, a highly-pure (fluoroaryl)borane compound can be stored (preserved) in a stable manner by adding the stabilizer to the (fluoroaryl)borane compound. More specifically, for example, the decomposition reaction can be suppressed while a solution of the (fluoroaryl)borane compound is heated and concentrated, stored (preserved) over a long period, or transported/transferred, thereby making it possible to stabilize the (fluoroaryl)borane compound readily at low costs.

The hydrocarbon solvent used in the stabilizing and crystallizing methods of the present invention is not especially limited as long as being a solvent which dissolves the (fluoroaryl)borane compound but does not dissolve the inorganic metal salts, and is mainly composed of a non-aqueous solvent inactive to the stabilizing and crystallizing methods of the present invention. The hydrocarbon solvent may include other kinds of solvents.

Examples of the hydrocarbon solvent include, but not limited to:

a straight-chain, branched-chain, or cyclic aliphatic hydrocarbon, such as pentane, isopentane, hexane, cyclohexane, methyl cyclohexane, heptane, octane, nonane, decane, undecane, dodecane, tridecane, tetradecane, pentadecane, hexadecane, octadecane, paraffin, and petroleum ether;

aromatic hydrocarbon, such as benzene, toluene, o-xylene, m-xylene, p-xylene, 1,2,3-trimethylbenzene, 1,2,4-trimethylbenzene, 1,2,5-trimethylbenzene, 1,3,5-trimethylbenzene, ethyl benzene, propylbenzene, and butylbenzene; etc. The aliphatic hydrocarbon and aromatic hydrocarbon may additionally include a functional group inactive to the stabilizing and crystallizing methods of the present invention. One member or a mixture of two or more members selected from these example hydrocarbon solvents can be used effectively. Of all these examples, hexane, cyclohexane, methylcyclohexane, heptane, octane, IsoparE of Exxon Corp. (a mixture of isoparaffins having approximately 10 carbon atoms), nonane, decane, octadecane, etc. are suitable.

Although the percentage varies with a combination of the (fluoroaryl)borane compound and hydrocarbon solvent, temperature and the like, at least some percent of the (fluoroaryl)borane compound dissolves into the hydrocarbon solvent. An amount of the (fluoroaryl)borane compound contained in the hydrocarbon solvent, that is, a concentration, is not especially limited, but a higher concentration is preferable to store (preserve) or transport/transfer the (fluoroaryl)borane compound more efficiently. A preferable range is between 0.5 wt % and 50 wt %, and a more preferable range is between 1 wt % and 30 wt %. In addition, the (fluoroaryl)borane compound may be contained in the hydrocarbon solution in the form of slurry.

In the stabilizing method of the present invention, the inorganic metal salts are let coexist with the (fluoroaryl)borane compound in the hydrocarbon solution. Also, in the preserving and transporting methods of the present invention, the hydrocarbon solution containing the (fluoroaryl)borane compound is preserved or transported in the presence of the inorganic metal salts, which do not dissolve into the hydrocarbon solvent. Thus, the inorganic metal salts exist in the hydrocarbon solution as insoluble product (solid) deposited or dispersed therein. A method of letting the inorganic metal salts coexist with the (fluoroaryl)borane compound in the hydrocarbon solution, that is, a method of letting the (fluoroaryl)borane compound and inorganic metal salts coexist in the hydrocarbon solution is not especially limited, and examples of which are: a method of dissolving the (fluoroaryl)borane compound into the hydrocarbon solvent while suspending the inorganic metal salts in the solvent; a method of letting the hydrocarbon solvent contain slurry of the (fluoroaryl)borane compound and the inorganic metal salts; etc.

A temperature while the hydrocarbon solution is stored (preserved) or transported/transferred is not especially limited, and can be set adequately depending on the kinds of the (fluoroaryl)borane compounds and hydrocarbon solvents, a boiling point of the hydrocarbon solvent, etc. However, a temperature up to 200° C. is preferable; a range between −50° C. and 150° C. is more preferable and a range between −20° C. and 100° C. is most preferable. This is because, if the hydrocarbon solution is to be stored (preserved) or transported/transferred above 200° C., a heating apparatus and a cooling apparatus for refluxing the hydrocarbon solvent are additionally required to maintain such a high temperature, which is disadvantageous in terms of industrial use. Further, a pressure while the hydrocarbon solution is stored (preserved) or transported/transferred is not especially limited either, and the hydrocarbon solution can be stored (preserved) or transported/transferred under a normal (ambient), reduced, or increased pressure.

As has been explained, the stabilizing method of the present invention is a method of letting the inorganic metal salts coexist with the (fluoroaryl)borane compound in the hydrocarbon solution, according to which a highly-pure (fluoroaryl)borane compound can be stabilized. More specifically, for example, the decomposition reaction can be suppressed while a solution of the (fluoroaryl)borane compound is heated and concentrated, stored (preserved) over a long period, or transported/transferred, thereby making it possible to stabilize the (fluoroaryl)borane compound readily at low costs.

Also, as has been explained, the preserving and transporting methods of the present invention are the methods of preserving or transporting the hydrocarbon solution containing the (fluoroaryl)borane compound in the presence of the inorganic metal salts, according to which a highly-pure (fluoroaryl)borane compound can be preserved or transported. In other words, the decomposition reaction can be suppressed, thereby making it possible to preserve or transport the (fluoroaryl)borane compound readily at low costs.

In the crystallizing method of the present invention, the (fluoroaryl)borane compound is crystallized out of the hydrocarbon solution containing the (fluoroaryl)borane compound by concentrating the solution in the presence of the inorganic metal salts first and thence removing the inorganic metal salts. To be more specific, for example, the hydrocarbon solution is heated and concentrated in the presence of the inorganic metal salts first and thence the inorganic metal salts are removed, after which the solution is cooled to crystallize the (fluoroaryl)borane compound.

A temperature when concentrating the hydrocarbon solution is not especially limited as long as it is at or above a boiling point of the hydrocarbon solvent under the current pressure (concentrating pressure). Also, a pressure when concentrating the hydrocarbon solution is not especially limited either, and the hydrocarbon solution can be concentrated under a normal (ambient), reduced, or increased pressure. In case that a mixed hydrocarbon solvent is used, the boiling point is defined as the lowest boiling point among the boiling points of all the compounds included.

A concentration of the (fluoroaryl)borane compound in the concentrated solution is not especially limited, and can be set adequately depending on the solubility of the (fluoroaryl)borane compound. However, to remove the inorganic metal salts efficiently, it is preferable that the (fluoroaryl)borane compound is dissolved into the hydrocarbon solvent by the time the inorganic metal salts are removed. To be more specific, when the (fluoroaryl)borane compound is taken out from the hydrocarbon solution, a preferable concentration is a concentration at which the (fluoroaryl)borane compound is not crystallized at a temperature after the concentration but is crystallized when the solution is cooled.

In the crystallizing method of the present invention, the (fluoroaryl)borane compound is crystallized out of the hydrocarbon solution, containing the (fluoroaryl)borane compound and inorganic metal salts and having been preserved and transported by the above preserving and transporting methods, by cooling the solution after the inorganic metal salts are removed. When the hydrocarbon solution contains slurry of the (fluoroaryl)borane compound, the (fluoroaryl)borane compound is dissolved by heating the solution or adding an adequate amount of the hydrocarbon solvent first and thence the inorganic metal salts are removed, after which the solution is cooled. To remove the inorganic metal salts efficiently, it is preferable to dissolve the (fluoroaryl)borane compound into the hydrocarbon solvent by the time the inorganic metal salts are removed.

A temperature of the cooled hydrocarbon solution is not especially limited as long as it is at or above the melting point of the hydrocarbon solution. However, to crystalize a larger amount of the (fluoroaryl)borane compound, a temperature up to 50° C. is preferable. A temperature up to 20° C. is more preferable, and a temperature up to 10° C. is most preferable. A pressure when cooling the hydrocarbon solution is not especially limited, and the hydrocarbon solution can be cooled under a normal (ambient), reduced, or increased pressure.

When the (fluoroaryl)borane compound is crystallized, the inorganic metal salts can be removed from the hydrocarbon solution by filtration or the like right before the (fluoroaryl)borane compound is used. When the (fluoroaryl) borane compound is crystallized to be taken out after the hydrocarbon solution is heated and concentrated, the inorganic metal salts can be removed from the solution by filtration while the solution is heated at a temperature such that does not allow the (fluoroaryl)borane compound to crystalize. Further, when the (fluoroaryl)borane compound is crystallized to be taken out after the hydrocarbon solution is cooled, the inorganic metal salts can be removed from the solution by filtration or the like at a temperature such that does not allow the (fluoroaryl)borane compound to crystallize. A filtration method is not especially limited, and examples of which are filtration under reduced pressure, filtration under an increased pressure, etc. In short, the inorganic metal salts are removed from the hydrocarbon solution by the time the (fluoroaryl)borane compound is crystallized.

If the inorganic metal salts are removed by the filtration or the like when the (fluoroaryl)borane compound is not dissolved into the hydrocarbon solvent completely, an undissolved part of the (fluoroaryl)borane compound is undesirably removed with the inorganic metal salts. For this reason, it is preferable that the (fluoroaryl)borane compound is dissolved into the hydrocarbon solvent completely when the inorganic metal salts are removed. Note that, however, in case that the inorganic metal salts are recycled as the stabilizer or the (fluoroaryl)borane compound removed with the inorganic metal salts is collected, the (fluoroaryl)borane compound does not have to be dissolved into the hydrocarbon solvent completely when the inorganic metal salts are removed. Here, a method of removing the inorganic metal salts from the hydrocarbon solution is not especially limited.

As has been explained, the crystallizing method of the present invention is a method of crystallizing the (fluoroaryl)borane compound out of the hydrocarbon solution containing the (fluoroaryl)borane compound by concentrating the solution in the presence of the inorganic metal salts first and thence removing the inorganic metal salts. Also, as has been explained, the crystallizing method of the present invention is a method of crystallizing the (fluoroaryl)borane compound out of the hydrocarbon solution containing the (fluoroaryl)borane compound and inorganic metal salts, which has been preserved and transported by the above preserving and transporting methods, by cooling the solution after having removed the inorganic metal salts.

Consequently, the decomposition reaction of the (fluoroaryl)borane compound can be suppressed, thereby making it possible to isolate highly-pure crystals (powders) of the (fluoroaryl)borane compound readily and efficiently at low costs. A purity of the crystals of the (fluoroaryl)borane compound obtained by either method of the present invention is preferably 90 wt % or above, more preferably 95 wt % or above, and most preferably 97 wt % or above. Since the crystallized (fluoroaryl)borane compound can be handled in the form of solid, not only the handling property during the storage (preservation) or transportation/transfer can be improved, but also the costs of storage (preservation) or transportation can be saved compared with the conventional case where the (fluoroaryl)borane compound is handled in the form of a solution.

The isolating manipulation for crystallizing the (fluoroaryl)borane compound out of the hydrocarbon solution from which the inorganic metal salts have been removed can be repeated as many times as necessary. More specifically, for example, after the crystals of the (fluoroaryl) borane compound are filtered out, the filtrate may be cooled, so that the (fluoroaryl)borane compound dissolved in the filtrate is crystallized, after which the filtrate is subjected to filtration again.

The (fluoroaryl)borane compound stabilized or crystallized by the methods of the present invention, especially tris(pentafluorophenyl)borane, is useful as a co-catalyst for promoting the activity of the metallocene catalyst (polymeric catalyst).

In the following, the present invention will be explained in detail by way of examples and comparative examples, but the present invention is not limited to the disclosure below.

EXAMPLE 1

To begin with, a hydrocarbon solution containing the (fluoroaryl)borane compound is prepared. More specifically, air inside a 4-neck flask equipped with a thermometer, a dropping funnel, a stirrer, a nitrogen gas conduit, and a reflux condenser and having a capacity of 200 ml is displaced by a nitrogen gas three times. Then, 2.976 g (122.4 millimole) of shavings of magnesium and 100 ml of diethyl ether are charged to the flask. Meanwhile, 29.35 g (118.8 millimole) of bromopentafluorobenzene is charged to the dropping funnel.

Then, bromopentafluorobenzene is dropped over two hours or so at room temperature while diethyl ether is stirred under a nitrogen gas atmosphere. During the dropping, a temperature inside the flask rises to 38° C. When the dropping ends, the reaction solution is let undergo maturation for three hours at room temperature with stirring under a nitrogen gas atmosphere, whereby a diethyl ether solution of pentafluorophenyl magnesium bromide is obtained at the yield of 97.5%.

Subsequently, air inside a 4-neck flask equipped with a thermometer, a dropping funnel, a stirrer, a nitrogen gas conduit, and a reflux condenser and having a capacity of 300 ml is displaced by a nitrogen gas in a satisfactory manner. Then, 5.454 g (38.43 millimole) of a boron trifluoride diethyl ether complex and 100 ml of diethyl ether are charged to the flask. Meanwhile, the diethyl ether solution of pentafluorophenyl magnesium bromide obtained in the above manner is charged to the dropping funnel.

Then, the diethyl ether solution is dropped over 30 minutes or so at room temperature while the content in the flask is stirred under a nitrogen gas atmosphere. During the dropping, a temperature inside the flask rises to 40° C. When the dropping ends, the reaction solution is let under go reaction (maturation) with stirring for three hours at a refluxing temperature, that is, 37° C., whereby a diethyl ether solution of tris(pentafluorophenyl)borane is obtained as the (fluoroaryl)borane compound. The solution is analyzed under predetermined conditions using $^{19}$F-NMR, and the reaction yield of tris(pentafluorophenyl)borane thus found is 93.15%.

Then, 750 ml of IsoparE (name of merchandise) serving as the hydrocarbon solvent is charged to a 4-neck flask equipped with a thermometer, a dropping funnel, a stirrer, and a Liebig condenser and having a capacity of 1 L. The outlet end of the Liebig condenser is kept open and a receiver is placed at a predetermined position. Meanwhile, the diethyl ether solution of tris(pentafluorophenyl)borane obtained in the above manner is charged to the dropping funnel.

Then, after IsoparE is heated to 80° C. with the stirring, the diethyl ether solution in the dropping funnel is dropped while diethyl ether is distilled out under a normal pressure. When the dropping ends, the distillation of the solvent containing diethyl ether is stopped when a temperature inside the flask rises to 125° C.

Then the content is filtered with heating to remove the deposit, that is, magnesium bromide fluoride produced as a by-product, whereby an IsoparE solution of tris (pentafluorophenyl)borane is obtained as the filtrate. The filtrate is analyzed under predetermined conditions using $^{19}$F-NMR, and the yield and purity of tris (pentafluorophenyl)borane thus found are 91.7% and 96.7%, respectively.

Then, 30.0 g of the hydrocarbon solution containing the (fluoroaryl)borane compound prepared in the above manner, that is, the IsoparE solution of tris(pentafluorophenyl)borane (concentration: 2.89 wt %, an amount of tris (pentafluorophenyl)borane contained: 1.69 millimole), is placed in a lidded vessel made of synthetic resin and having a capacity of 250 ml. Then, 0.217 g (1.76 millimole) of magnesium bromide fluoride serving as the stabilizer (inorganic metal salts) is added to the solution, after which the solution is allowed to stand for 192 hours at room temperature.

Subsequently, the solution is analyzed under predetermined conditions using $^{19}$F-NMR, and the yield and purity of tris(pentafluorophenyl)borane thus found are 86.6% and 81.8%, respectively.

EXAMPLE 2

An IsoparE solution of tris(pentafluorophenyl)borane is obtained by carrying out the reaction and manipulation in the same manner as Example 1 above.

Then, 100 g of the IsoparE solution (concentration: 3.06 wt %, an amount of tris(pentafluorophenyl)borane contained: 5.98 millimole) and 0.755 g (6.13 millimole) of magnesium bromide fluoride serving as the stabilizer (inorganic metal salts) are charged to a 4-neck flask equipped with a thermometer, a stirrer, and a Liebig condenser and having a capacity of 200 ml. The outlet end of the Liebig condenser is kept open and a receiver is placed at a predetermined position.

Then, IsoparE is distilled out under a normal pressure while the content is heated with stirring, and the distillation is stopped when an amount of the distillate amounts to 75.3 g. A temperature inside the flask at this point is 125° C.

Then, the content is subjected to suction filtration with heating at 100° C. to remove magnesium bromide fluoride. When the filtrate is cooled, tris(pentafluorophenyl)borane is crystallized out of the filtrate. The crystals are filtered out and dried under a reduced pressure at room temperature, whereby powders of tris(pentafluorophenyl)borane are isolated. The powders are analyzed under predetermined conditions using $^{19}$F-NMR, and the yield and purity of tris (pentafluorophenyl)borane thus found are 79.4% and 95.0%, respectively. The filtrate is analyzed in the same manner as above, and the recovery percentage of tris (pentafluorophenyl)borane thus found is 80.2%.

EXAMPLE 3

An IsoparE solution of tris(pentafluorophenyl)borane is obtained by carrying out the reaction and manipulation in the same manner as Example 1 above.

Then, 100 g of the IsoparE solution (concentration: 3.06 wt %, an amount of tris(pentafluorophenyl)borane contained: 5.98 millimole) and 0.16 g (6.17 millimole) of lithium fluoride serving as the stabilizer (inorganic metal salts) are charged to a 4-neck flask equipped with a thermometer, a stirrer, and a Liebig condenser and having a capacity of 200 ml. The outlet end of the Liebig condenser is kept open and a receiver is placed at a predetermined position.

Then, IsoparE is distilled out under a normal pressure while the content is heated with stirring, and the distillation is stopped when an amount of distillate amounts to 76.1 g. A temperature inside the flask at this point is 126° C.

Then, the content is subjected to suction filtration with heating at 100° C. to remove lithium fluoride. When the filtrate is cooled, tris(pentafluorophenyl)borane is crystallized out of the filtrate. The crystals are filtered out, and dried under a reduced pressure at room temperature, whereby powders of tris(pentafluorophenyl)borane are isolated. The powders are analyzed under predetermined conditions using $^{19}$F-NMR, and the yield and purity of tris (pentafluorophenyl)borane thus found are 80.6% and 94.9%, respectively. The filtrate is analyzed in the same manner as above and the recovery percentage of tris (pentafluorophenyl) borane thus found is 81.1%.

EXAMPLE 4

Here, 0.217 g (1.76 millimole) of magnesium bromide fluoride is removed by suction filtration from 30.0 g of the IsoparE solution of tris(pentafluorophenyl)borane (concentration: 2.50 wt %, an amount of tris (pentafluorophenyl) borane contained: 1.47 millimole), which is in effect the solution allowed to stand for 192 hours at room temperature in Example 1 above.

Then, the filtrate is cooled for 30 minutes at –60° C. using a dry ice-methanol bath, whereby crystals of tris (pentafluorophenyl)borane are obtained. The crystals are filtered out and dried at room temperature under a reduced pressure, whereby powders of tris(pentafluorophenyl)borane are isolated. The powders are analyzed under predetermined conditions using $^{19}$F-NMR, and the yield and purity of tris(pentafluorophenyl)borane thus found are 54.9% and 94.3%, respectively. The filtrate is analyzed in the same manner and the recovery percentage of tris (pentafluorophenyl)borane thus found is 60.1%.

EXAMPLE 5

Here, 30.0 g of IsoparE solution of tris (pentafluorophenyl)borane (concentration: 3.56 wt %, an amount of tris(pentafluorophenyl)borane contained: 2.08 millimole) is prepared in the same manner as Example 1 above, and charged to a lidded vessel made of synthetic resin and having a capacity of 250 ml. Then, 0.310 g (2.50 millimole) of magnesium bromide fluoride is added to the solution, after which the solution is allowed to stand for 450 hours at room temperature.

Subsequently, magnesium bromide fluoride is removed from the solution through filtration under reduced pressure. Then, the filtrate is cooled for 60 minutes at –60° C. using a dry ice-methanol bath, whereby crystals of tris (pentafluorophenyl)borane are obtained. The crystals are filtered out and dried at room temperature under a reduced pressure, whereby powders of tris(pentafluorophenyl)borane are isolated. The powders are analyzed under predetermined conditions using $^{19}$F-NMR, and the yield and purity of tris(pentafluorophenyl)borane thus found are 82.5% and 95.0%, respectively. Also, the filtrate is analyzed in the same manner as above and the recovery percentage of tris (pentafluorophenyl) borane thus found is 89.1%.

COMPARATIVE EXAMPLE 1

Here, 30.0 g of the IsoparE solution of tris (pentafluorophenyl) borane (concentration: 2.89 wt %, an amount of tris(pentafluorophenyl)borane contained: 1.69 millimole) prepared in Example 1 above is placed in a lidded vessel made of synthetic resin and having a capacity of 250 ml. Then, the solution is allowed to stand for 192 hours at room temperature. In other words, the solution is allowed to stand without adding the stabilizer.

Then, the solution is analyzed under predetermined conditions using $^{19}$F-NMR, and the yield and purity of tris (pentafluorophenyl)borane thus found are 65.5% and 62.4%, respectively.

COMPARATIVE EXAMPLE 2

An IsoparE solution of tris(pentafluorophenyl)borane is obtained by carrying out the reaction and manipulation in the same manner as Example 1 above.

Then, 100 g of the IsoparE solution (concentration: 3.06 wt %, an amount of tris(pentafluorophenyl)borane contained: 5.98 millimole) is charged to a 4-neck flask equipped with a thermometer, a stirrer, and a Liebig condenser and having a capacity of 200 ml. The outlet end of the Liebig condenser is kept open, and a receiver is placed at a predetermined position.

Then, IsoparE is distilled out while the content is stirred with heating. In other words, IsoparE is distilled out without adding the stabilizer to the solution. The distillation of IsoparE is stopped when an amount of distillate amounts to 68.4 g. A temperature inside the flask at this point is 127° C.

The content is cooled and the crystals of tris (pentafluorophenyl) borane are obtained. The crystals are filtered out and dried at room temperature under a reduced pressure, whereby powders of tris(pentafluorophenyl)borane are isolated. The powders are analyzed under predetermined conditions using $^{19}$F-NMR, and the yield and purity of tris(pentafluorophenyl)borane thus found are 39.3% and 98.0%, respectively. The filtrate is analyzed in the same manner, and the recovery percentage of tris (pentafluorophenyl)borane is 67.8%.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of stabilizing a (fluoroaryl)borane compound expressed by General Formula (1):

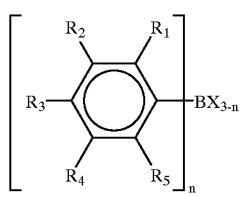

where each of $R_1$, $R_2$, $R_3$, $R_4$ and $R_5$ represents one of a hydrogen atom, a fluorine atom, a hydrocarbon group, and an alkoxy group, provided that at least one of $R_1$–$R_5$ represents a fluorine atom, X represents one of a fluorine atom, a chlorine atom, a bromine atom, and an iodine atom, and n represents one of 2 and 3, wherein said method consists essentially of mixing an inorganic metal salt having a fluorine atom to said (fluoroaryl)borane compound in a hydrocarbon solution.

2. The method of claim 1 wherein said inorganic metal salt having a fluorine atom contains a fluorine atom and at least one inorganic metal selected from the group consisting of lithium, beryllium, magnesium, aluminum, potassium, calcium, titanium, vanadium, chromium, manganese, iron, cobalt, nickel, copper, zinc, gallium, germanium, strontium, yttrium, zirconium, niobium, molybdenum, silver, cadmium, indium, tin, antimony, tellurium, cesium, barium, cerium, osmium, iridium, mercury and lead.

3. The method of claim 2, wherein said inorganic metal salt is one of lithium fluoride and magnesium bromide fluoride.

4. The method of claim 2 wherein said inorganic metal salt is present in a mole ratio of said inorganic metal salt to said (fluoroaryl)borane compound of between 0.7 and 5.0 inclusive.

5. The method of claim 2 wherein said (fluoroaryl)borane compound is tris(pentafluorophenyl)borane.

6. A method of preserving and transporting a (fluoroaryl) borane compound comprising combining an isolated (fluoroaryl)borane compound of the Formula (1):

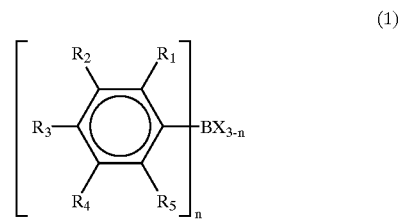

where each of $R_1$, $R_2$, $R_3$, $R_4$, and $R_5$ represents one of a hydrogen atom, a fluorine atom, a hydrocarbon group, and an alkoxy group, provided that at least one of $R_1$–$R_5$ represents a fluorine atom, X represents one of a fluorine atom, a chlorine atom, a bromine atom, and an iodine atom, and n represents one of 2 and 3, and a hydrocarbon solution with an inorganic metal salt comprising a fluorine atom prior to said transporting.

7. The method of claim 6 wherein said inorganic metal salt having a fluorine atom contains a fluorine atom and at least one inorganic metal selected from the group consisting of lithium, beryllium, magnesium, aluminum, potassium, calcium, titanium, vanadium, chromium, manganese, iron, cobalt, nickel, copper, zinc, gallium, germanium, strontium, yttrium, zirconium, niobium, molybdenum, silver, cadmium, indium, tin, antimony, tellurium, cesium, barium, cerium, osmium, iridium, mercury and lead.

8. The method of claim 7, wherein said inorganic metal salt is one of lithium fluoride and magnesium bromide fluoride.

9. The method of claim 7 wherein said inorganic metal salt is present in a mole ratio of said inorganic metal salt to said (fluoroaryl)borane compound of between 0.7 and 5.0 inclusive.

10. The method of claim 7 wherein said (fluoroaryl) borane compound is tris(pentafluorophenyl)borane.

11. A method of crystallizing a (fluoroaryl)borane compound from the hydrocarbon solution of claim 6, which contains the (fluoroaryl)borane compound and an inorganic metal salt having a fluorine atom, said method comprising crystallizing the (fluoroaryl)borane compound from said solution by cooling said solution after having removed said inorganic metal salt.

* * * * *